(12) United States Patent
Jones et al.

(10) Patent No.: US 8,784,442 B2
(45) Date of Patent: Jul. 22, 2014

(54) METHODS AND SYSTEMS FOR PERFORMING THROMBECTOMY PROCEDURES

(75) Inventors: Donald K Jones, Dripping Springs, TX (US); Vladimir Mitelberg, Austin, TX (US)

(73) Assignee: Empirilon Technology, LLC, Dripping Springs, TX (US)

( * ) Notice: Subject to any disclaimer, the term of this patent is extended or adjusted under 35 U.S.C. 154(b) by 0 days.

(21) Appl. No.: 13/589,133

(22) Filed: Aug. 18, 2012

(65) Prior Publication Data
US 2013/0046332 A1 Feb. 21, 2013

Related U.S. Application Data

(60) Provisional application No. 61/525,362, filed on Aug. 19, 2011.

(51) Int. Cl.
- *A61B 17/22* (2006.01)
- *A61M 29/02* (2006.01)
- *A61M 25/10* (2013.01)

(52) U.S. Cl.
CPC ...... *A61B 17/22032* (2013.01); *A61M 25/1002* (2013.01)
USPC ............................. 606/159; 606/127; 606/194

(58) Field of Classification Search
CPC ....................... A61M 25/1002; A61B 17/22032
USPC ........... 606/159, 194, 127; 604/96.01, 103.05
See application file for complete search history.

(56) References Cited

U.S. PATENT DOCUMENTS

| | | | |
|---|---|---|---|
| 4,318,410 A * | 3/1982 | Chin | 606/194 |
| 4,762,130 A | 8/1988 | Fogarty et al. | |
| 4,998,919 A | 3/1991 | Schnepp-Pesch et al. | |
| 5,108,406 A | 4/1992 | Lee | |
| 5,217,484 A | 6/1993 | Marks | |
| 5,222,973 A | 6/1993 | Sharpe et al. | |
| 5,304,183 A | 4/1994 | Gourlay et al. | |
| 5,364,345 A * | 11/1994 | Lowery et al. | 604/96.01 |
| 5,387,219 A | 2/1995 | Rappe | |
| 5,417,703 A | 5/1995 | Brown et al. | |
| 5,782,747 A | 7/1998 | Zimmon | |
| 5,840,043 A | 11/1998 | Palmer et al. | |
| 5,868,754 A | 2/1999 | Levine et al. | |
| 5,910,144 A | 6/1999 | Hayashi | |
| 6,663,650 B2 | 12/2003 | Sepetka et al. | |
| 6,673,100 B2 | 1/2004 | Diaz et al. | |
| 6,989,020 B2 | 1/2006 | Jones et al. | |
| 7,473,266 B2 | 1/2009 | Glaser | |
| 7,549,974 B2 * | 6/2009 | Nayak | 604/96.01 |
| 8,298,244 B2 | 10/2012 | Garcia et al. | |
| 2004/0181252 A1 * | 9/2004 | Boyle et al. | 606/194 |
| 2010/0036312 A1 | 2/2010 | Krolik et al. | |

* cited by examiner

*Primary Examiner* — Kathleen Holwerda
*Assistant Examiner* — Sarah W Aleman
(74) *Attorney, Agent, or Firm* — Donald K. Jones (57) ABSTRACT

Devices, systems and methods are provided for performing intra-lumenal medical procedures in a desired area of the body. Thrombectomy systems and methods of performing medical procedures to re-establish the intravascular flow of blood are provided for the treatment of ischemic disease states.

20 Claims, 5 Drawing Sheets

METHODS AND SYSTEMS FOR PERFORMING THROMBECTOMY PROCEDURES

CROSS-REFERENCE TO RELATED APPLICATIONS

This application claims the benefit of U.S. Prov. Ser. 61/525,362 filed Aug. 19, 2011 which is hereby incorporated by reference herein in its entirety.

BACKGROUND OF THE INVENTION

The field of intralumenal therapy for the treatment of vascular disease states has for many years focused on the use of many different types of therapeutic devices. While it is currently unforeseeable that one particular device will be suitable to treat all types of vascular disease states, it may however be possible to reduce the number of devices used for some disease states while at the same time improve patient outcomes at a reduced cost. To identify potential opportunities to improve the efficiency and efficacy of the devices and procedures it is important for one to understand the state of the art relative to some of the more common disease states.

For instance, one aspect of cerebrovascular disease in which the wall of a blood vessel becomes weakened. Under cerebral flow conditions the weakened vessel wall forms a bulge or aneurysm which can lead to symptomatic neurological deficits or ultimately a hemorrhagic stroke when ruptured. Once diagnosed a small number of these aneurysms are treatable from an endovascular approach using various embolization devices. These embolization devices include detachable balloons, coils, polymerizing liquids, gels, foams, stents and combinations thereof.

The most widely used embolization devices are detachable embolization coils. These coils are generally made from biologically inert platinum alloys. To treat an aneurysm, the coils are navigated to the treatment site under fluoroscopic visualization and carefully positioned within the dome of an aneurysm using sophisticated, expensive delivery systems. Typical procedures require the positioning and deployment of multiple embolization coils which are then packed to a sufficient density as to provide a mechanical impediment to flow impingement on the fragile diseased vessel wall. Some of these bare embolization coil systems have been describe in U.S. Pat. No. 5,108,407 to Geremia, et al., entitled, "Method And Apparatus For Placement Of An Embolic Coil" and U.S. Pat. No. 5,122,136 to Guglielmi, et al., entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils at predetermined positions within vessels of the human body in order to treat aneurysms, or alternatively, to occlude the blood vessel at a particular location. Many of these systems, depending on the particular location and geometry of the aneurysm, have been used to treat aneurysms with various levels of success. One drawback associated with the use of bare embolization coils relates to the inability to adequately pack or fill the aneurysm due to the geometry of the coils which can lead to long term recanalization of the aneurysm with increased risk of rupture.

Some improvements to bare embolization coils have included the incorporation of expandable foams, bioactive materials and hydrogel technology as described in the following U.S. Pat. No. 6,723,108 to Jones, et al., entitled, "Foam Matrix Embolization Device", U.S. Pat. No. 6,423,085 to Murayama, et al., entitled, "Biodegradable Polymer Coils for Intraluminal Implants" and U.S. Pat. No. 6,238,403 to Greene, et al., entitled, "Filamentous Embolic Device with Expansible Elements." While some of these improved embolization coils have been moderately successful in preventing or reducing the rupture and re-rupture rate of some aneurysms, the devices have their own drawbacks. For instance, in the case of bioactive coils, the materials eliciting the biological healing response are somewhat difficult to integrate with the coil structure or have mechanical properties incompatible with those of the coil making the devices difficult to accurately position within the aneurysm. In the case of some expandable foam and hydrogel technology, the expansion of the foam or hydrogel is accomplished due to an interaction of the foam or hydrogel with the surrounding blood environment. This expansion may be immediate or time delayed but is generally, at some point, out of the control of the physician. With a time delayed response the physician may find that coils which were initially placed accurately and detached become dislodged during the expansion process leading to subsequent complications.

For many aneurysms, such as wide necked or fusiform aneurysms the geometry is not suitable for coiling alone. To somewhat expand the use of embolization coils in treating some wide necked aneurysms, stent like scaffolds have been developed to provide support for coils. These types of stent like scaffolds for use in the treatment of aneurysms have been described in U.S. Pat. No. 6,605,111 to Bose et al., entitled, "Endovascular Thin Film Devices and Methods for Treating Strokes" and U.S. Pat. No. 6,673,106 to Mitelberg, et al., entitled, "Intravascular Stent Device". While these stent like devices have broadened the types of aneurysms amenable to embolization therapy, utilization of these devices in conjunction with embolization devices is technically more complex for the physician, may involve more risk to the patient and have a substantial cost increase for the healthcare system.

To further expand the types of aneurysm suitable for interventional radiological treatment, improved stent like devices have been disclosed in U.S. Pat. No. 5,824,053 to Khosravi et al., entitled, "Helical Mesh Endoprosthesis and Method", U.S. Pat. No. 5,951,599 to McCrory, entitled, "Occlusion System for the Endovascular Treatment of and Aneurysm" and U.S. Pat. No. 6,063,111 to Hieshima et al., entitled, "Stent Aneurysm Treatment System and Method." When placed across the neck of an aneurysm the proposed stent like devices purport to have a sufficient density through the wall of the device to reduce flow in the aneurysm allowing the aneurysm to clot, while at the same time having a low enough density through the wall to allow small perforator vessels adjacent to the aneurysm to remain patent. Stent devices of this nature while having the potential to reduce treatment costs have not been realized commercially due to the difficulty in manufacturing, reliability in delivering the devices to the treatment site and an inability to properly position the denser portion of the stent device accurately over the neck of the aneurysm.

Another cerebrovascular disease state is ischemia resulting from reduced or blocked arterial blood flow. The arterial blockage may be due to thrombus, plaque, foreign objects or a combination thereof. Generally, soft thrombus created elsewhere in the body (for example due to atrial fibrillation) that lodges in the distal cerebrovasculature may be disrupted or dissolved using mechanical devices and or thrombolytic drugs. While guidewires are typically used to disrupt the thrombus, some sophisticated thrombectomy devices have been proposed. For instance U.S. Pat. No. 4,762,130 to Fogarty et al., entitled, "Catheter with Corkscrew-Like Balloon", U.S. Pat. No. 4,998,919 of Schepp-Pesh et al., entitled, "Thrombectomy Apparatus", U.S. Pat. No. 5,417,703 to Brown et al., entitled "Thrombectomy Devices and Methods of Using Same", and U.S. Pat. No. 6,663,650 to Sepetka et al., entitled, "Systems, Methods and Devices for Removing Obstructions from a Blood Vessel" discloses devices such as catheter based corkscrew balloons, baskets or filter wires and helical coiled retrievers. Commercial and prototype versions of these devices have shown only marginal improvements over guidewires due to an inability to adequately grasp the thrombus or to gain vascular access distal to the thrombus (i.e. distal advancement of the device pushes the thrombus distally).

Plaque buildup within the lumen of the vessel, known as atherosclerotic disease, is not generally responsive to thrombolytics or mechanical disruption using guidewires. The approach to the treatment of neurovascular atherosclerotic disease has been to use modified technology developed for the treatment of cardiovascular atherosclerotic disease, such as balloons and stents, to expand the vessel at the site of the lesion to re-establish blood flow. For instance, U.S. Pat. No. 4,768,507 to Fischell et al., entitled, "Intravascular Stent and Percutaneous Insertion Catheter System for the Dilation of an Arterial Stenosis and the Prevention of Arterial Restenosis" discloses a system used for placing a coil spring stent into a vessel for the purposes of enhancing luminal dilation, preventing arterial restenosis and preventing vessel blockage resulting from intimal dissection following balloon and other methods of angioplasty. The coil spring stent is placed into spiral grooves on an insertion catheter. A back groove of the insertion catheter contains the most proximal coil of the coil spring stent which is prevented from springing radially outward by a flange. The coil spring stent is deployed when an outer cylinder is moved proximally allowing the stent to expand. Other stent systems include those disclosed in U.S. Pat. No. 4,512,338 to Balko, et al., entitled, "Process for Restoring Patency to Body Vessels", U.S. Pat. No. 5,354,309 to Schnepp Pesch et al., entitled, "Apparatus for Widening a Body Cavity" and U.S. Pat. No. 6,833,003 to Jones et al., entitled, "Expandable Stent and Delivery System". While the aforementioned devices may have the ability to access the cerebrovasculature, they lack sufficient structural coverage of the lesion to achieve the desired patency of the vessel without the use of a balloon device.

SUMMARY OF THE INVENTION

In accordance with one aspect of the present invention there is provided a medical device system for restoring patency of a body lumen in a mammal. The thrombectomy system includes a thrombectomy catheter having proximal and distal ends including a proximal hub, a balloon member having proximal and distal ends, including a longitudinally extending portion and a radially expanding retrieval portion, where the balloon member proximal end is coupled to the catheter distal end and an inflation source member coupled to the proximal hub. The extending portion of the balloon member has an inflated diameter which is smaller than the inflated diameter of the retrieval portion. An elongate tether member is positioned within the catheter lumen and preferably coupled to the balloon member distal end. The tether member extends proximally through the thrombectomy catheter lumen and proximal to the proximal end of the hub assembly.

For delivery to a desired target site, the balloon member is everted and positioned within the lumen of the thrombectomy catheter such that the distal end of the balloon member is proximal to the distal end of the catheter. The balloon member of the delivery catheter is typically formed of a thin walled polymeric tube in which the distal end of the tube has been enlarged and sealed and the proximal end of the balloon member is coupled to the distal end of the catheter such that the lumen of the catheter is in fluid communication with the interior surface of the balloon. The balloon member is preferably formed of a high strength non-compliant polymeric material such as nylon, polyester and others, however, metallic materials such as thin-film nitinol or other alloys may also be suitable. The inflation source member is coupled to the proximal end of the catheter and used to apply fluid pressure to the lumen of catheter at a level sufficient to cause the balloon member extending portion to extend longitudinally from the catheter lumen and subsequently deploy and expand the capture portion of the balloon member. The preferred fluids include liquids such as saline although gases such as carbon dioxide gas may be suitable for some system configurations. The amount of fluid pressure required to inflate the balloon member is related to the friction force between the balloon member inner surface and the interior wall of the catheter lumen. The inflation source member preferably takes the form of a syringe (threaded or non-threaded), however other inflation sources such as a pressurized fluid source having a valve assembly or a controllable fluid delivery pump are also suitable.

In accordance with another aspect of the present invention there is provided a balloon member for a thrombectomy system having a longitudinally extending portion formed of a non-compliant material and a radially expanding retrieval portion formed of a compliant material. Suitable compliant materials include polymeric elastomers such as silicones, urethanes, polyether block amide (PEBAX) and synthetic rubbers including polyisoprene, nitrile, chloroprene and ethylene propylene diene rubber.

In accordance with another aspect of the present invention there is provided a balloon member for a thrombectomy system having a longitudinally extending portion and a radially expanding retrieval portion coupled to a thrombectomy catheter where the inflated diameter of the extending portion is larger than the outer diameter of the thrombectomy catheter.

In accordance with another aspect of the present invention there is provided a balloon member for a thrombectomy system having a longitudinally extending portion and a radially expanding retrieval portion coupled to a thrombectomy catheter where the inflated diameter of the extending portion is smaller than the outer diameter of the thrombectomy catheter.

DETAILED DESCRIPTION OF THE INVENTION

Figure 1:
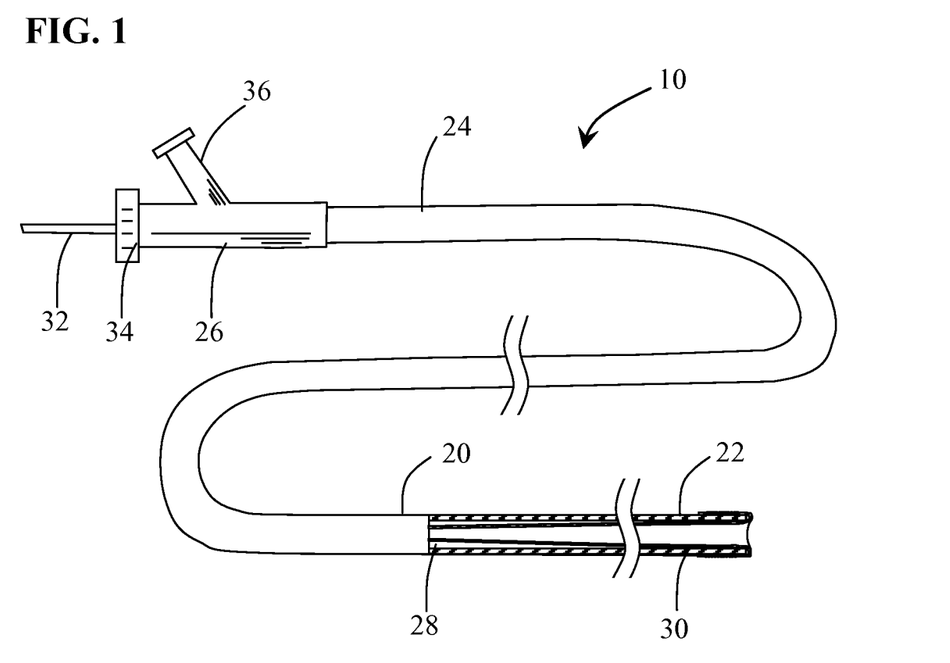
FIG. 1 is a partial cross-sectional view of a thrombectomy system according to an embodiment of the present invention.

Methods and systems for capturing and removing an embolus or thrombus from an area of the body are herein described. While the terms "thrombectomy" and "thrombus" generally refer to removal of a specific type of embolus, the usage herein should be considered more broadly to include the removal additional types of emboli such as plaque, solid tissue fragments, clots and foreign objects that may block or restrict the normal flow of blood within the vasculature. FIG. 1 illustrates a thrombectomy system 10 according to an embodiment of the present invention. Thrombectomy system 10 includes an elongate catheter 20 having distal end 22, proximal end 24 including hub member 26 and lumen 28 extending therethrough. Coupled to distal end 22 of catheter 20 is balloon member 30. An elongate flexible tether member 32 coupled to balloon member 30 is slidably positioned within lumen 28 and extends through hub member 26. Balloon member 30 has a delivery configuration in which it is everted and positioned within lumen 28 of catheter 20 at distal end 22. Proximal end 24 of catheter 20 is coupled to hub member 26 which includes sealable valve 34 and inflation port 36.

Figure 2A:
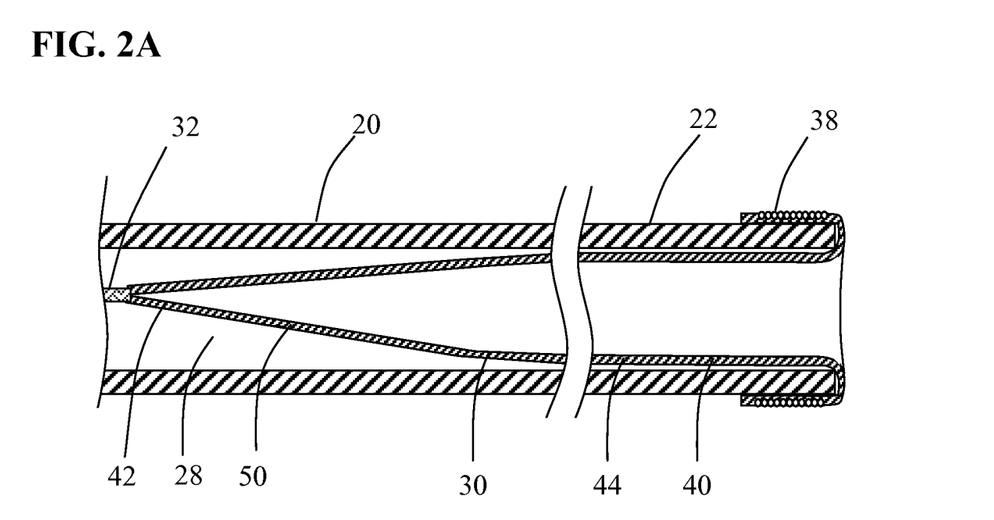
FIG. 2A is an enlarged partial cross-sectional view of the distal end of the thrombectomy system according to an embodiment of the present invention.

A partial cross sectional view of distal end 22 of catheter 20 is shown in FIG. 2A. While not shown, the construction of catheter 20 may utilize known catheter technologies that incorporate braiding and or coiling using metallic or non-metallic reinforcing filamentous materials to provide high strength while maintaining catheter flexibility. The incorporation of lubricious hydrophilic and or hydrophobic materials on the inner and or outer surface of the catheter is considered to be within the scope of known catheter construction techniques and suitable for use in a thrombectomy system according to embodiments of the present invention. Retaining member 38 is used to affix proximal end 40 of balloon member 30 to catheter distal end 22. The inner diameter of balloon member proximal end 40 is slightly larger than the outer diameter of catheter distal end 22 thereby allowing distal end 22 to be inserted within proximal end 40. Retaining member 38 is shown as a flexible filament (preferably polymeric) wound around proximal end 40 and catheter distal end 22 securing balloon member 30 to catheter 20. Balloon member proximal end 40 and distal end 22 may be secured using other means such as heat fusing, multifilament winds, ultrasonic welding and or gluing to insure a good bond and seal. The distal end 42 of balloon member 30 is completely sealed using any of the aforementioned techniques and positioned everted within catheter lumen 28 proximal to balloon member proximal end 40. Balloon member 30 includes a proximally located longitudinally extending portion 44 and a distally located radially expanding retrieval portion 50.

Figure 2B:
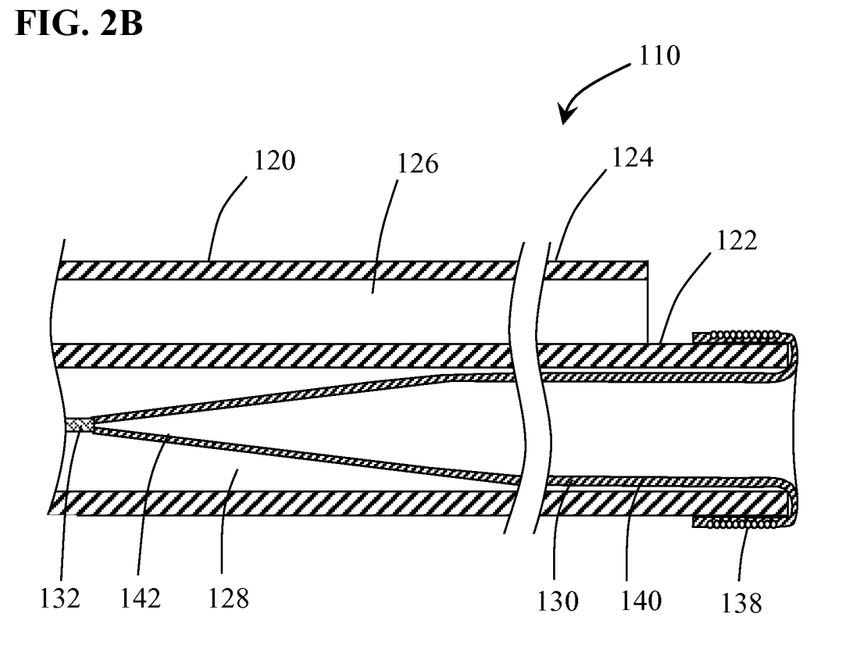
FIG. 2B is an enlarged partial cross-sectional view of the distal end of a thrombectomy system according to another embodiment of the present invention.

FIG. 2B illustrates an alternate embodiment of the present invention showing thrombectomy system 110. Thrombectomy system 110 includes an elongate catheter 120 having delivery portion 122 and guidewire portion 124. Guidewire portion 124 having through lumen 126 extends proximally to the proximal end of catheter 120. Alternatively guidewire portion 124 and lumen 126 may extend proximally only a portion of the length of catheter 120 and have a configuration suitable for use as a "rapid exchange" system allowing system 110 to reach a target site over a guidewire that has already been positioned at the target site. Delivery portion 122 includes lumen 128 extending from the proximal end to the distal end of catheter 120. An elongate flexible tether member 132 is coupled to balloon member 130 and extends proximally through catheter lumen 128. Securing member 138, shown as a wound filament, affixes balloon member proximal end 140 to the distal end of delivery portion 122. Balloon member proximal end 140 and the distal end of delivery portion 122 may be secured using other means such as heat fusing, ultrasonic welding, multifilament winds and or gluing to insure a good bond and seal. The distal end 142 of balloon member 130 is completed sealed using any of the aforementioned techniques and positioned everted within catheter lumen 128 proximal to proximal end 140.

Figure 3A:
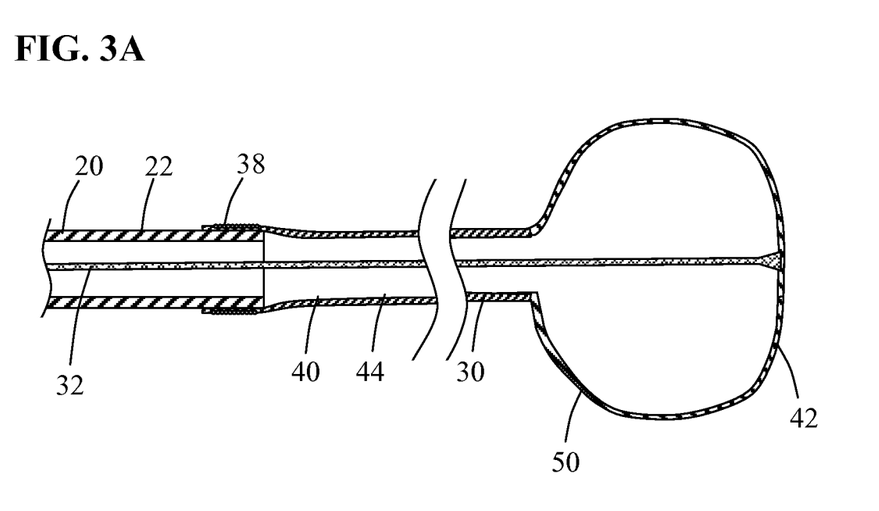
FIG. 3A is a partial cross sectional view of a deployed thrombectomy system according to an embodiment of the present invention.

FIG. 3A shows an enlarged partial cross sectional view of the distal portion of thrombectomy system 10 including catheter 20 having distal end 22. Balloon member 30 is shown in an inflated configuration longitudinally extending distal to catheter distal end 22. In this configuration, balloon member distal end 42 is positioned distal to balloon member proximal end 40. Extending portion 44 of balloon member 30 has a diameter slightly smaller than catheter 20 and ranges from about 0.4 to about 0.99 times the diameter of catheter 20 and has a preferred range from about 0.5 to 0.9 times the diameter of catheter 20. Typically, the expanded diameter of retrieval portion 50 is slightly larger than the inner diameter of the vessel at a target site to insure that the retrieval portion stays in contact with the vessel wall during the thrombus removal process. Balloon member 30 is typically formed of a thin walled polymeric tube having a proximal non-compliant portion defining extending portion 44 coupled to a distal compliant portion defining retrieval portion 50 that has been sealed. The tube portions may be joined using known joining techniques such as, thermal fusing, ultrasonic welding, gluing, and solvent bonding. Suitable materials for the extending portion of balloon member 30 include high strength non-compliant polymeric material such as nylon, polyester and others, however, metallic materials such as thin-film nitinol or other alloys may also be suitable. Suitable materials for the retrieval portion 50 of balloon member 30 includes compliant polymeric elastomers such as silicones, urethanes, polyether block amide (PEBAX) and synthetic rubbers including polyisoprene, nitrile, chloroprene and ethylene propylene diene rubber.

Figure 3B:
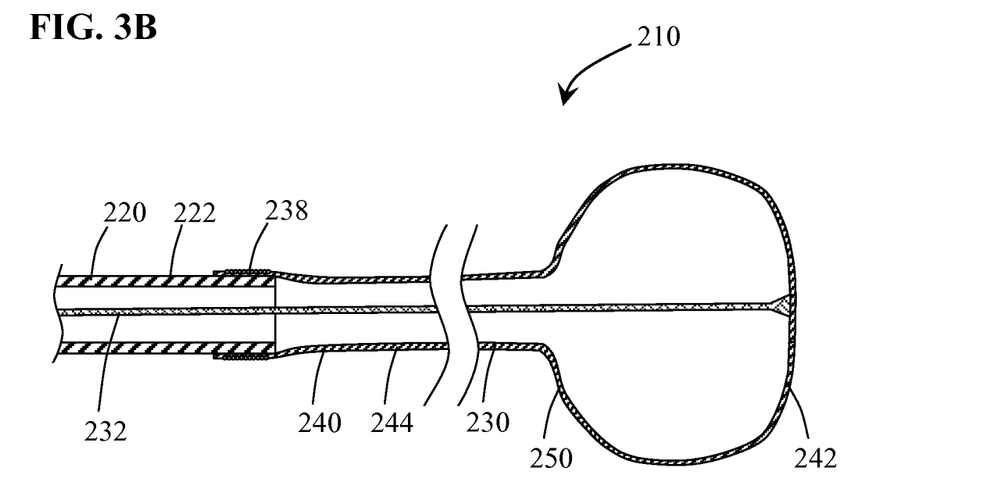
FIG. 3B is a partial cross sectional view of a deployed thrombectomy system according to another embodiment of the present invention.
Figure 3C:
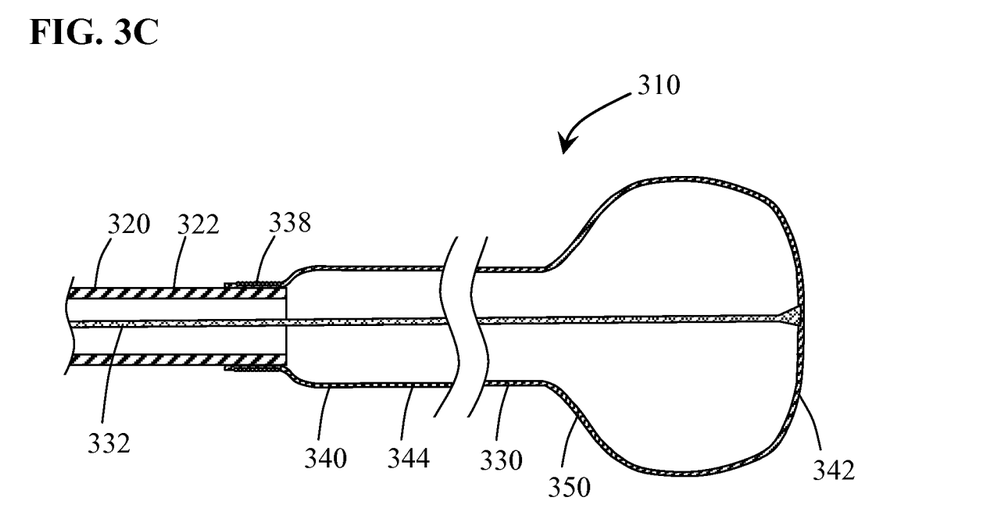
FIG. 3C is a partial cross sectional view of a deployed thrombectomy system according to yet another embodiment of the present invention.

FIGS. 3B and 3C are partial cross sectional views of thrombectomy systems according to alternate embodiments of the present invention that illustrate different configurations of inflated extended balloon members. FIG. 3B shows an enlarged partial cross sectional view of the distal portion of thrombectomy system 210 including catheter 220 having distal end 222. Balloon member 230 is shown in an inflated configuration longitudinally extending distal to catheter distal end 222. In this configuration, balloon member distal end 242 is positioned distal to balloon member proximal end 240. Extending portion 244 of balloon member 230 has a diameter slightly smaller than catheter 220 and ranges from about 0.4 to about 0.99 times the diameter of catheter 220 and has a preferred range from about 0.5 to 0.9 times the diameter of catheter 220. Typically, the expanded diameter of retrieval portion 250 is slightly larger than the inner diameter of the vessel at a target site to insure that the retrieval portion stays in contact with the vessel wall during the thrombus removal process. Balloon member 230 is typically formed of a thin walled polymeric tube in which the distal end of the tube has been enlarged and sealed. Balloon member 230 is preferably formed of a high strength non-compliant polymeric material such as nylon, polyester and others, however, metallic materials such as thin-film nitinol or other alloys may also be suitable.

FIG. 3C shows an enlarged partial cross sectional view of the distal portion of thrombectomy system 310. Balloon member 330 is shown in an inflated configuration longitudinally extending distal to catheter distal end 322. In this configuration, balloon member distal end 342 and retrieval portion are positioned distal to balloon member proximal end 340 and extending portion 344. Extending portion 344 of balloon member 330 has a diameter slightly larger than catheter 320 and ranges from about 1.0 to about 1.5 times the diameter of catheter 320 and has a preferred range from about 1.05 to 1.3 times the diameter of catheter 320. Typically, the expanded diameter of retrieval portion 350 is slightly larger than the inner diameter of the vessel at a target site to insure that the retrieval portion stays in contact with the vessel wall during the thrombus removal process. Balloon member 330 is typically formed of a thin walled polymeric tube in which the distal end of the tube has been enlarged and sealed. Balloon member 330 is preferably formed of a high strength non-compliant polymeric material such as nylon, polyester and others, however, metallic materials such as thin-film nitinol or other alloys may also be suitable.

Figure 4A:
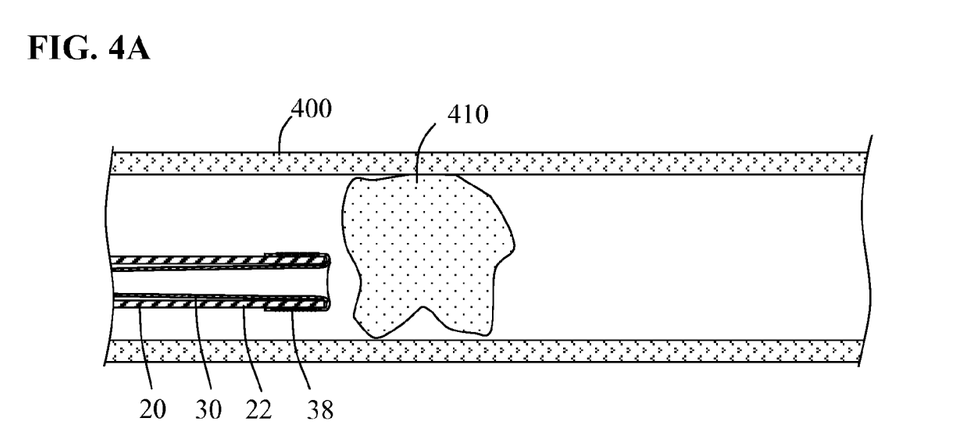
FIGS. 4A through 4F partial cross-sectional views illustrating a method of delivering and deploying a thrombectomy system within a vessel at a target site according to an embodiment of the present invention.
Figure 4B:
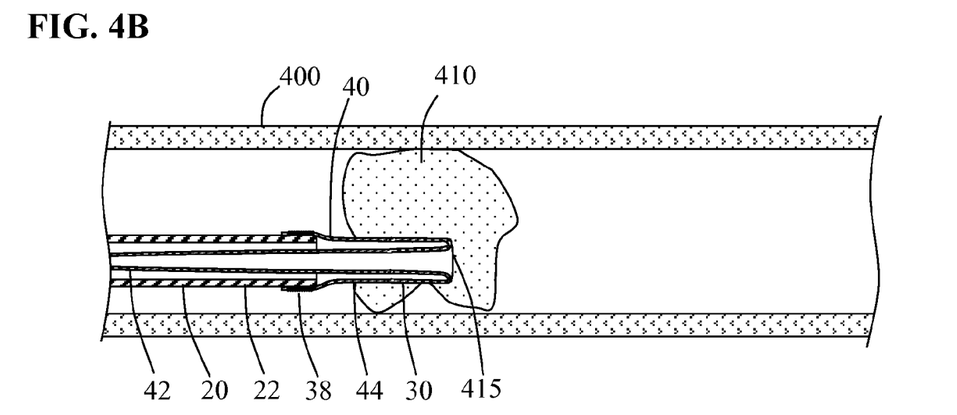
Figure 4C:
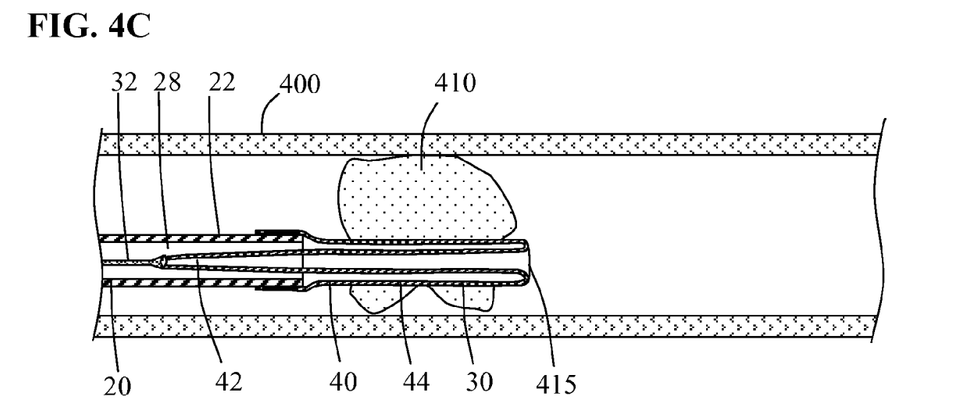
Figure 4D:
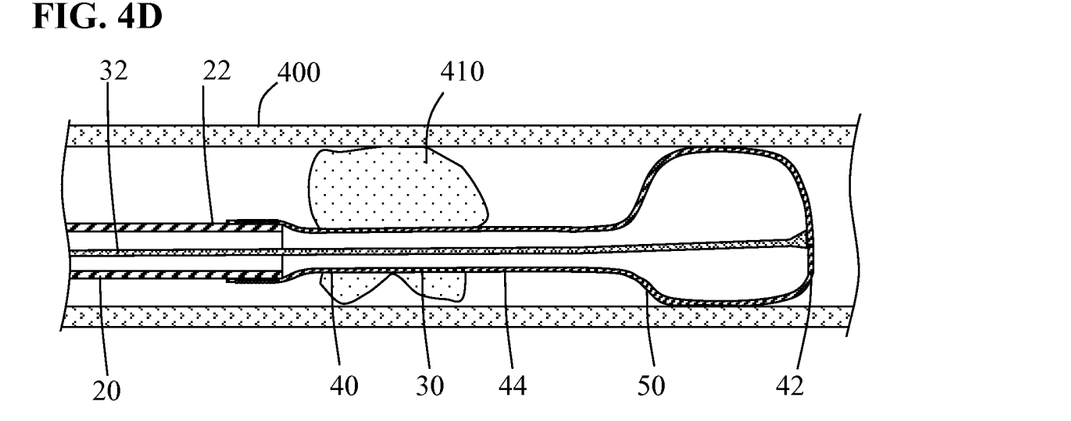
Figure 4E:
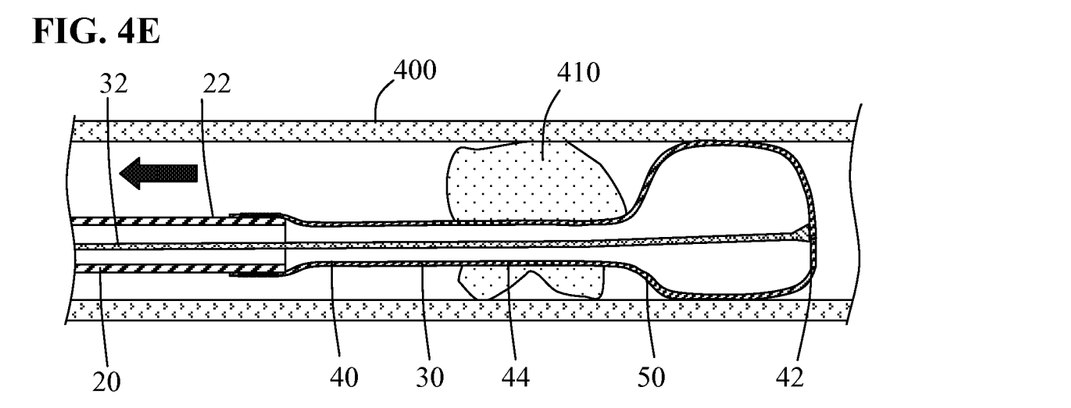
Figure 4F:
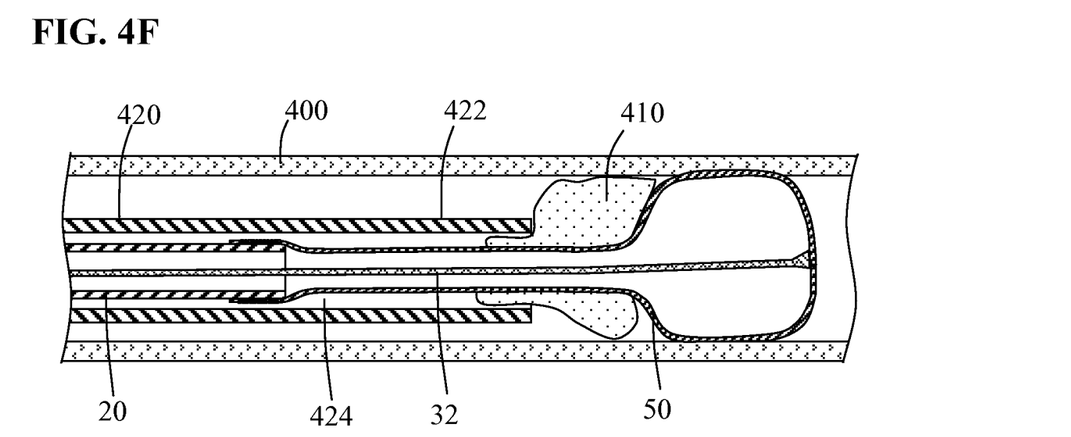

FIGS. 4A through 4F illustrate a method of deploying a retrieval assembly at a target site within a body lumen according to one embodiment of the present invention. The thrombectomy system 10 is positioned within a vessel 400. Catheter distal end 22 including extendable balloon member 30 are positioned at a target site adjacent to thrombus 410. An inflation source member (not shown) is coupled to the proximal end of the catheter 20 and used to apply fluid pressure to the lumen of catheter. The inflation source member preferably takes the form of a syringe (threaded or non-threaded), however other inflation sources such as a pressurized fluid source having a valve assembly or a controllable fluid delivery pump are also suitable. The preferred fluids include liquids such as saline and radiopaque contrasts solutions however gases such as carbon dioxide gas may be suitable for some system configurations. As the applied fluid pressure increases to a sufficient level, balloon member 30 begins to extend longitudinally from the catheter lumen. As balloon member 30 extends longitudinally from catheter 20, leading edge 415 of the balloon member 30 may encounter thrombus 410. While shown as large particle, thrombus 410 may have a varied composition that could comprise organized clot, tissue, plaque soft clot or even foreign objects. Dependant somewhat upon the size and composition of thrombus 410 balloon member 30 may extend longitudinally through a soft and compliant thrombus or between the inner vessel wall and a more rigid thrombus. Leading edge 415 of balloon member 30 is well suited to extend longitudinally between the more rigid thrombus and the vessel wall without perforating the vessel. With continued application of fluid pressure, balloon member 30 continues to extend longitudinally until retrieval 50 is deployed and positioned distal to thrombus 410. Once retrieval portion 50 is appropriately deployed, application of additional fluid pressure is unnecessary. As shown in FIG. 4E, thrombectomy system 10 including tether member 32 is pulled proximally causing retrieval portion 50 to engage the distal side of thrombus 410. Tether member 32 ensures that sufficient retraction force is applied directly to retrieval portion 50 to move thrombus 410. Thrombectomy system 10 with thrombus 410 may then be removed from the body. Alternatively, thrombectomy system 10 with captured thrombus 410 may be pulled proximally within larger catheter 420 having distal end 422 and lumen 424. Suction may then be applied to lumen 424 thus aiding retention of thrombus 410 during removal or to fragment and remove thrombus 410.

Novel devices, systems and methods have been disclosed to re-establish flow in a lumen of mammal. Although preferred embodiments of the invention have been described, it should be understood that various modifications including the substitution of elements or components which perform substantially the same function in the same way to achieve substantially the same result may be made by those skilled in the art without departing from the scope of the claims which follow.

What is claimed is:

1. A thrombus removal system for use within the vasculature of a mammal comprising:
    an elongate tubular flexible member having proximal and distal ends and a lumen extending therethrough;
    a balloon member having proximal and distal ends, an elongate extended portion positioned adjacent said proximal end and a retrieval portion positioned adjacent said extended portion and said distal end wherein said proximal end of said balloon member is secured to the distal end of said flexible member,
    an elongate flexible tether member slidably positioned within the lumen of said flexible member and having proximal and distal ends wherein the distal end of said tether member is coupled to the distal end of said balloon member,
    said balloon member being operable by fluid pressure between a first configuration where said balloon member is collapsed and the distal end of said balloon member is everted and positioned within the lumen of said flexible member proximal to the proximal end of said balloon member and a second configuration where said balloon member is inflated and the distal end of said balloon member is positioned distal to the distal end of said flexible member such that when in said second configuration said extended portion has a longitudinal length and an unconstrained expanded diameter which is generally constant along said longitudinal length and said longitudinal length is substantially greater than said diameter and is positioned distal to the distal end of said flexible member and said retrieval portion is positioned distal to said extended portion and has a diameter which is substantially greater than the diameter of said extended portion and a longitudinal length which is substantially smaller than the longitudinal length of said extended portion.

2. The thrombus removal system of claim 1 further comprising an elongate tubular catheter having proximal and distal ends and a lumen extending therethrough, said flexible member being slidably positioned within the lumen of said catheter such that when said flexible member distal end is positioned distal to said catheter distal end and said balloon member is in said second configuration, said flexible member distal end and said extended portion may be retracted to position said flexible member distal end and said extended portion within the lumen of said catheter distal end.

3. The thrombus removal system of claim 2 wherein the diameter of said extended portion in said second configuration is smaller than the diameter of said flexible member.

4. The thrombus removal system of claim 1 wherein said balloon member includes a non-compliant material.

5. The thrombus removal system of claim 1 wherein said balloon member includes a compliant material.

6. The thrombus removal system of claim 1 wherein said balloon member comprises a metallic thin film.

7. The thrombus removal system of claim 1 wherein the diameter of said extended portion in said second configuration is smaller than the diameter of said flexible member.

8. The thrombus removal system of claim 1 wherein the diameter of said extended portion in said second configuration is larger than the diameter of said flexible member.

9. The thrombus removal system of claim 1 wherein the diameter of said retrieval portion in said second configuration is larger than twice the diameter of said extended portion in said second configuration.

10. A thrombus removal system for use within the vasculature of a mammal comprising:
an elongate tubular flexible member having proximal and distal ends and a lumen extending therethrough;
an elongate balloon member having a proximal end fixedly attached to the distal end of said flexible member and a distal end which is closed and unattached to the distal end of said flexible member, said balloon member having an elongate first portion positioned adjacent said proximal end and a second portion positioned adjacent said first portion and said balloon member distal end, said balloon member having a first configuration in which said balloon member is collapsed and inverted and the distal end of said balloon member is positioned within the lumen at the distal end of said flexible member and a second configuration in which said balloon member is inflated and the distal end of said balloon member is positioned distal to the lumen at the distal end of said flexible member and said first portion has a longitudinal length and an unconstrained inflated diameter which is generally constant along said longitudinal length and said longitudinal length is substantially greater than said diameter and said second portion is positioned distal to said first portion and has a diameter which is substantially greater than the diameter of said first portion and,
an elongate flexible tether member slidably positioned within the lumen of said flexible member and having proximal and distal ends wherein the distal end of said tether member is coupled to the distal end of said balloon member,
said balloon member being operable by fluid pressure to transition said balloon member from said first configuration to said second configuration such that when said balloon member is in said first configuration and fluid pressure is applied to the lumen of said flexible member positioned proximal to a thrombus in a vessel, said first portion exits from the lumen of the flexible member and extends distally such that said balloon member second portion is positioned distal to the thrombus and inflated to said second configuration.

11. The thrombus removal system of claim 10 further comprising an elongate tubular catheter having proximal and distal ends and a lumen extending therethrough, said flexible member being slidably positioned within the lumen of said catheter such that when said flexible member distal end is positioned distal to said catheter distal end and said balloon member is in said second configuration, said flexible member distal end and said first portion may be retracted to position said flexible member distal end and said first portion within the lumen of said catheter distal end.

12. The thrombus removal system of claim 11 wherein the diameter of said first portion in said second configuration is smaller than the diameter of said flexible member.

13. The thrombus removal system of claim 10 wherein said balloon member includes a non-compliant material.

14. The thrombus removal system of claim 10 wherein said balloon member includes a compliant material.

15. The thrombus removal system of claim 10 wherein said balloon member comprises a metallic thin film.

16. The thrombus removal system of claim 10 wherein the diameter of said first portion in said second configuration is smaller than the diameter of said flexible member.

17. The thrombus removal system of claim 10 wherein the diameter of said first portion in said second configuration is larger than the diameter of said flexible member.

18. The thrombus removal system of claim 10 wherein the diameter of said second portion in said second configuration is larger than twice the diameter of said first portion in said second configuration.

19. A thrombus removal system for use within the vasculature of a mammal comprising:
an elongate tubular flexible member having proximal and distal ends and a lumen extending therethrough;
an elongate balloon member having a proximal end fixedly attached to the distal end of said flexible member and a distal end which is closed and unattached to the distal end of said flexible member, said balloon member having an elongate first portion positioned adjacent said proximal end and a second portion positioned adjacent said first portion and said balloon member distal end, said balloon member having a first configuration in which said balloon member is collapsed and inverted and the distal end of said balloon member is positioned within the lumen at the distal end of said flexible member and a second configuration in which said balloon member is inflated and the distal end of said balloon member is positioned distal to the lumen at the distal end of said flexible member and said first portion has a longitudinal length and an unconstrained expanded diameter which is generally constant along said longitudinal length and said longitudinal length is substantially greater than said diameter and said second portion is positioned distal to said first portion and has a diameter which is substantially greater than the diameter of said first portion and said second portion has a longitudinal length which is substantially smaller than the longitudinal length of said first portion and,
an elongate flexible tether member slidably positioned within the lumen of said flexible member and having proximal and distal ends wherein the distal end of said tether member is coupled to the distal end of said balloon member,
said balloon member being operable by fluid pressure to transition said balloon member from said first configuration to said second configuration such that when said balloon member is in said first configuration and fluid pressure is applied to the lumen of said flexible member positioned proximal to a thrombus in a vessel, said first portion exits from the lumen of the flexible member and extends distally such that said balloon member second portion is positioned distal to the thrombus and inflated to said second configuration.

20. The thrombus removal system of claim 19 further comprising an elongate tubular catheter having proximal and distal ends and a lumen extending therethrough, said flexible member being slidably positioned within the lumen of said catheter such that when said flexible member distal end is positioned distal to said catheter distal end and said balloon member is in said second configuration, said flexible member distal end and said first portion may be retracted to position said flexible member distal end and said first portion within the lumen of said catheter distal end.

* * * * *